(12) United States Patent
Nelson

(10) Patent No.: US 7,120,487 B2
(45) Date of Patent: Oct. 10, 2006

(54) CATHETER SYSTEM AND METHOD FOR ADMINISTERING REGIONAL ANESTHESIA TO A PATIENT

(76) Inventor: David A. Nelson, 8004 Danforth Cove, Austin, TX (US) 78746

( * ) Notice: Subject to any disclaimer, the term of this patent is extended or adjusted under 35 U.S.C. 154(b) by 364 days.

(21) Appl. No.: 10/623,488

(22) Filed: Jul. 18, 2003

(65) Prior Publication Data
US 2004/0073159 A1   Apr. 15, 2004

(51) Int. Cl.
*A61N 1/30* (2006.01)
(52) U.S. Cl. .................. 604/21; 604/158; 604/512; 604/167.01
(58) Field of Classification Search ............ 604/19–21, 604/158, 272, 506–508, 500, 512, 167.01–167.06, 604/164.07, 93.01
See application file for complete search history.

(56) References Cited

U.S. PATENT DOCUMENTS

| | | | |
|---|---|---|---|
| 3,081,770 A | 3/1963 | Hunter | |
| 3,682,162 A * | 8/1972 | Colyer | 600/373 |
| 3,709,211 A | 1/1973 | Hawkins | |
| 3,977,400 A | 8/1976 | Moorehead | |
| 4,580,573 A | 4/1986 | Quinn | |
| 4,775,637 A | 10/1988 | Schmidt | |
| 4,917,668 A | 4/1990 | Haindl | |
| 4,917,670 A | 4/1990 | Hurley et al. | |
| 4,958,901 A | 9/1990 | Coombs | |
| 4,994,036 A | 2/1991 | Biscoping et al. | |
| 5,004,456 A | 4/1991 | Botterbusch et al. | |
| 5,007,902 A | 4/1991 | Witt | |
| 5,024,655 A * | 6/1991 | Freeman et al. | 604/509 |
| 5,085,631 A | 2/1992 | Leighton | |
| 5,106,376 A | 4/1992 | Mononen et al. | |
| 5,119,832 A | 6/1992 | Xavier | |
| 5,135,525 A | 8/1992 | Biscoping et al. | |
| 5,312,374 A | 5/1994 | Gurmarnik | |
| 5,328,479 A | 7/1994 | Gurmarnik | |
| 5,405,334 A * | 4/1995 | Roth et al. | 604/264 |
| 5,417,208 A | 5/1995 | Winkler | |
| 5,512,052 A | 4/1996 | Jesch | |
| 5,630,802 A | 5/1997 | Moellmann et al. | |
| 5,976,110 A * | 11/1999 | Greengrass et al. | 604/158 |
| 6,004,293 A | 12/1999 | Bell | |
| 6,179,828 B1 | 1/2001 | Mottola et al. | |
| 6,190,370 B1 | 2/2001 | Tsui | |
| 6,193,704 B1 | 2/2001 | Winters | |
| 6,298,256 B1 * | 10/2001 | Meyer | 600/373 |
| 6,363,273 B1 * | 3/2002 | Mastrorio et al. | 600/434 |
| 6,925,333 B1 * | 8/2005 | Krebs | 607/116 |

FOREIGN PATENT DOCUMENTS

DE    20018216    2/2002
EP     0966922    12/1999

* cited by examiner

*Primary Examiner*—Nicholas Lucchesi
*Assistant Examiner*—Theodore J. Stigell
(74) *Attorney, Agent, or Firm*—Charles D. Huston; Daffer McDaniel, LLP

(57) ABSTRACT

A catheter system and method is provided for overcoming various problems commonly associated with the application of regional anesthesia. Disclosed herein are several embodiments for providing continuous regional anesthesia. In general, the catheter system includes an epidural catheter, an epidural needle, tubing for optional fluid administration, an attached conductive wire (for connection to a nerve stimulator) and a catheter introducer, which is integrated within the proximal hub of the insulated needle. The embodiments may differ in several ways.

22 Claims, 10 Drawing Sheets

CATHETER SYSTEM AND METHOD FOR ADMINISTERING REGIONAL ANESTHESIA TO A PATIENT

BACKGROUND OF THE INVENTION

1. Field of the Invention

The present invention relates generally to the field of delivering continuous local anesthesia to peripheral nerves. More particularly, it concerns adaptations to a proximal hub of an insulated needle and a method for introducing an "epidural" style catheter through an insulated needle and adjacent to a desired peripheral nerve or nerve plexus in a reliable and safe manner.

2. Description of the Related Art

The following descriptions and examples are not admitted to be prior art by virtue of their inclusion within this section.

"Regional anesthesia" is a term generally used to describe the practice of rendering select parts (or regions) of the body insensate to painful stimuli. Currently, the most reliable means of achieving regional anesthesia is by application of a local anesthetic to a peripheral nerve or plexus of nerves. By doing so, a particular area is numbed to painful stimuli, which may occur during or after surgery, or from other forms of trauma.

During surgical procedures, it is often desirable to provide regional anesthesia on a continual basis as an infusion, particularly in the postoperative settings. By utilizing regional anesthesia instead of general anesthesia, the post-surgical patient can remain relatively pain-free without systemic side effects, such as nausea or drowsiness, that are generally associated with narcotics and other systemic analgesics.

A standardized medical procedure for providing regional anesthesia as a continuous infusion is the introduction of a peripheral nerve catheter adjacent to the desired nerve or nerve plexus. The term "epidural style" catheter may be alternately used to describe a peripheral nerve catheter. The most common method of localizing the desired nerve or nerve plexus is by applying milliamp levels of current to an insulated needle. The nerve is then located by gradually advancing the insulated needle until the applied current induces visible muscle contraction. In order to achieve muscle contraction, however, the tip of the insulated needle must be within millimeters of the nerve. This allows only a very small margin for error on the part of the anesthesiologist, and obviously to those skilled in the art, any movement of the needle could reduce the effect of the regional anesthetic, damage the nerve, or both.

Conventional catheter systems used for administering local anesthetic (otherwise referred to as "continuous nerve block systems" or "peripheral nerve catheter systems") are cumbersome and awkward to use in clinical practice. One example of a conventional peripheral nerve catheter system is described in U.S. Pat. No. 5,976,110 and shown in FIG. 1. In general, conventional peripheral nerve catheter system 100 includes a standard epidural catheter threading assist guide 110, which functions to stiffen an epidural catheter 150 so that it can puncture the hemostatic valve (not shown) incorporated within the body of a multipurpose connector 120. The multipurpose connector 120 includes a proximal end 122 adapted for receiving an epidural catheter 150, a distal end 126 adapted for connection to a proximal hub 135 of an insulated needle 130, and a middle aperture 124 adapted for fluid connection to a fluid source 170 via tubing 160. An electrically conductive stimulation wire 140 is coupled for applying a stimulating current to insulated needle 130, which is typically insulated with the exception of the tip of the needle.

However, system 100 suffers from many disadvantages. In particular, most clinicians find it difficult to hold the needle 130, the multipurpose connector 120, and the epidural catheter threading assist guide 110 in one hand 180, while threading the epidural catheter 150 with the other hand 190. To do so, without moving needle 130, provides another level of difficulty. Often, clinicians become frustrated with the multipurpose connector 120 and disconnect it entirely from the proximal hub 135 of insulated needle 130. In such cases, the epidural catheter threading assist guide 110 is inserted into the proximal hub 135 of the insulated needle 130 to assist in threading the epidural catheter 150. The process of removing the multipurpose connector 120 introduces another unnecessary source of potential movement of insulated needle 130. It is therefore desirable to provide a peripheral nerve catheter system that does not require the manipulations required by many of the prior art systems, so that movement of the indwelling needle and catheter is minimized.

Another disadvantage of system 100 is that the multipurpose connector's middle aperture 124 is placed at a 90-degree angle to the shaft of insulated needle 130. This configuration is generally disadvantageous because of the increased likelihood that tubing 160 will kink. In addition, the configuration severely limits the mobility of the system, and in some cases, introduces an additional source of movement for the indwelling needle, due to interference with adjacent anatomical structures. For example, the orthogonal configuration of middle aperture 124 may cause tubing 160 to catch on the patient's right ear during placement of the catheter in the right neck region. It is therefore desirable to provide a system for administering regional anesthesia that does not interfere with anatomical structures. It is a further object of the present invention to provide a system for administering regional anesthesia which, when inserted at a preferred location in a patient's body, does not require the person administering the anesthesia to contact anatomical structures on the patient.

Another disadvantage to system 100 is the likelihood that fluid will reflux out of the system during advancement and/or withdrawal of epidural catheter 150 through the proximal hub 135 of insulated needle 130. For example, if epidural catheter 150 is inserted while fluid is being administered through tubing 160, reflux of the fluid has been known to occur at the point where the epidural catheter penetrates the hemostatic valve within multipurpose connector 120. More specifically, the hemostatic valve may not, in all cases, provide a complete seal around the catheter as it is advanced into (or withdrawn out of) the multipurpose connector. It is therefore desirable to provide a system for administering regional anesthesia that prevents fluid reflux from occurring when epidural catheter 150 is moving (or stationary) within the proximal hub 135.

Multipurpose connector 120 is further described in the above-mentioned patent as an adapter, which must be manually attached to the proximal hub 135 before the epidural catheter can be inserted, and before fluid can be administered, to an indwelling needle. In this manner, fluid reflux may also occur at the interface between multipurpose connector 120 and the proximal hub 135 if multipurpose connector 120 is not properly and securely attached. Therefore, it is further desirable to provide a system for administering regional anesthesia that prevents fluid reflux resulting from the need to manually assemble system components.

FIGS. 2–5 illustrate another peripheral nerve catheter system 200 for administering continuous local anesthetic to peripheral nerves. In the system of FIG. 2, local anesthetic from fluid source 270 is administered through tubing 260 and down the long axis of an insulated needle 230. Similar to system 100, system 200 includes an electrically conductive stimulation wire 240 for applying current to insulated needle 230 for locating a desired nerve or plexus of nerves.

System 200, however, suffers from it's own share of disadvantages. In particular, tubing 260 must be unscrewed from the proximal hub 235 of insulated needle 230 to allow threading of epidural catheter 250. In other words, epidural catheter threading assist guide 210 may only be inserted through the proximal hub 235 of insulated needle 230 after tubing 260 is removed. FIG. 3 is a view of the catheter system of FIG. 2 illustrating the removal of tubing 260 in preparation for threading epidural catheter 250 through the proximal hub 235 of insulated needle 230. FIG. 4 is a view of insulated needle 230 with epidural threading assist guide 210 inserted into the proximal hub 235 of the insulated needle.

FIG. 5 illustrates the process of threading epidural catheter 250 through epidural catheter threading assist guide 210 and into insulated needle 230. As before, movement associated with the removal of tubing 260 may cause the insulated needle to become misplaced. In some cases, misplacement of the insulated needle may reduce the effectiveness of the local anesthetic or may increase the time needed for correctly positioning the epidural catheter. Misplacement of the needle may even cause nerve damage by directly contacting the nerve. Thus, a major disadvantage of system 200 results from the fact that tubing 260 must be disconnected from proximal hub 235 in order to connect catheter 250. In addition to tubing disconnections, system 200 requires manual insertion of thread guides (such as, e.g., catheter threading assist guide 210) for placing the epidural catheter within the patient. It is therefore desirable to provide a system for administering regional anesthesia without requiring disconnection of tubing (such as, e.g., tubing 260) or manual insertion of thread guides.

Regardless of whether system 100 or system 200 is used, there is a danger that the epidural catheter may kink during insertion through a hemostatic valve or a proximal hub. At best, a kinked catheter may be more difficult to thread through the insulated needle. In some situations, however, kinking of the catheter may occlude the orifice of the catheter (making it nearly impossible to administer anesthesia) or may cause a portion of the catheter to shear off into the patient (due to contact with a beveled edge of the needle tip). As such, anesthesiologists often find it safer to remove portions of the catheter system (e.g. multipurpose connector 120 of FIG. 1) to make it easier to thread the epidural catheter without the danger of kinking the catheter. It is therefore desirable to provide a system with features that reduce the dangers associated with threading the epidural catheter through the needle.

It is therefore desirable to provide a peripheral nerve catheter system with features that reduce or eliminate opportunities for an indwelling needle or catheter to move once the needle is near a nerve or nerve plexus.

SUMMARY OF THE INVENTION

The problems outlined above are in large part solved by an improved peripheral nerve catheter system for reliably and predictably placing an epidural catheter adjacent to a desired peripheral nerve or nerve plexus. Such a system may enable a clinician to thread an epidural catheter without risking excessive movement of the indwelling insulated needle. In addition, the system may allow a user (typically a clinician or anesthesiologist) to easily hold the insulated needle and integral threading assist guide in one hand, while threading the epidural catheter with the other hand. The system may also eliminate any necessity for removing components in order to thread the epidural catheter. As such, the system may be configured to minimize the likelihood of epidural catheter misplacement, thereby avoiding the problems associated therewith.

Thus, the present invention provides solutions to a variety of problems commonly associated with the application of regional anesthesia. Disclosed herein are several embodiments for providing continuous regional anesthesia. All embodiments include an epidural catheter, an insulated needle, attached tubing (for optional fluid administration), an attached conductive wire (for connection to a nerve stimulator) and a catheter threading assist guide, which is incorporated into the proximal hub of the insulated needle. The embodiments may differ in several ways.

In most embodiments, the catheter system includes an insulated needle having a proximal end and a distal end. In general, the proximal end of the insulated needle is configured for fluid connection, whereas the distal end is configured for insertion through tissue and into the vicinity of a nerve or plexus of nerves. The proximal end of the insulated needle may also be referred to as the "hub" of the needle. An electrically conductive wire may be coupled for supplying an electrical current to the insulated needle. In some cases, the insulated needle is a Tuohy type needle. In other cases, the insulated needle is a straight needle with varying degrees of beveling at the distal end.

In some embodiments, the catheter system may include a side port extending from a side surface of the proximal hub of the insulated needle at an acute angle from the longitudinal axis of the catheter system. Such a side port may include an integral catheter threading assist guide to facilitate threading of a catheter through the insulated needle. In some cases, the catheter may be configured for insertion through the side port and the insulated needle for administration of fluids within the vicinity of the nerve plexus.

In a broad respect, the present invention is directed to a system and method for preventing reflux of fluids during administration of regional anesthesia. As such, the catheter threading assist guide may, in some embodiments, include an end cap, which is coupled for sealing an orifice of the catheter threading assist guide against fluid leakage when the catheter is not arranged within the catheter threading assist guide. The end cap may include a flip-top style cap, a hinged style cap or a screw cap in various embodiments of the present invention. Unlike conventional catheter systems, a user of the present catheter system may easily remove the end cap with one hand while threading the catheter with the other hand. In other embodiments, however, the catheter threading assist guide may be integrated within the proximal hub of the insulated needle (in this case, within the side port). The advantages of such an embodiment will be described in more detail below.

In some embodiments, the catheter system may include a catheter introducer having a distal end and a proximal end. In a preferred embodiment of the present invention, the distal end of the catheter introducer is made integral with the proximal end (or hub) of the insulated needle. In some cases, the distal end of the catheter introducer may be attached to the proximal hub by an adhesive material. In other cases, however, the hub and the distal end of the catheter introducer are molded to form a single component of the catheter system. Likewise, the proximal end of the catheter introducer may include an integral threading assist guide to facilitate threading of the catheter through the catheter introducer and the insulated needle. Stated another way, the threading assist guide may be permanently attached to the upper aspect of the proximal hub of the insulated needle.

Thus, in a broad respect, one object of the invention is to incorporate a catheter threading assist guide into the proximal hub of the insulated needle. In a preferred embodiment of the present invention, the catheter threading assist guide is formed as an integral component of the proximal hub to provide a fixed path for threading the epidural catheter. In a narrow respect, the integral threading assist guide eliminates assembly related problems and prevents kinking of the epidural catheter during placement.

As noted above, one object of the invention is to prevent reflux of fluid administered through the insulated needle. In some embodiments, the invention may incorporate an end cap over the threading assist guide to prevent reflux of administered fluids, as described above. In a preferred embodiment, however, an integral threading assist guide includes a cap portion and an elastic tube. The cap portion may be in rotational securement with the distal end of the catheter introducer, whereas the elastic tube may be arranged about the rotational axis of the catheter threading assist guide. More specifically, the elastic tube may be fixedly attached to the cap portion and to the distal end of the catheter introducer, such that rotation of the cap portion relative to the distal end of the catheter introducer modifies an internal diameter of the elastic tube.

In some cases, rotation of the cap portion reduces the internal diameter to seal an orifice of the integral threading assist guide against fluid leakage when the catheter is not arranged within the catheter introducer. In other cases, however, rotation of the cap portion reduces the internal diameter to form a continuous, fluid-tight seal about an outer surface of the catheter. The integral threading assist guide may be configured for maintaining the continuous, fluid-tight seal about the catheter before, during and after the catheter is inserted therein. The integral threading assist guide may be further configured for maintaining the continuous, fluid-tight seal about an epidural or peripheral nerve catheter of substantially any size.

A method for administering local anesthetic or other fluids to a nerve, or plexus of nerves, within a patient is provided herein. In general, the method includes the step of providing a catheter system, such as the catheter system described above in various embodiments. Preferably, the catheter system utilized in the current method includes a catheter introducer (having a threading assist guide at one end thereof) that is made integral with the proximal end of the insulated needle. In some embodiments, the method may include the step of preloading a catheter within the catheter introducer and into the proximal end of the insulated needle. As used herein, the term "preloading" refers to the act of inserting the catheter into the catheter introducer and proximal hub before the insulated needle, or any other component of the catheter system, is inserted within the patient. In this manner, the present method provides a means for minimizing the movement of an indwelling needle during the step of threading of the catheter.

Before, during or after the step of preloading a catheter, the method may include the step of rotating a cap portion of the catheter introducer. After inserting the distal end of the insulated needle through the tissue of the patient, the method may further include the step of detecting when the distal end of the insulated needle is in the vicinity of a nerve or nerve plexus by supplying an electrical current to the insulated needle via an electrically conductive wire coupled thereto. To verify correct positioning of the distal end of the insulated needle relative to the nerve plexus, fluid is sometimes withdrawn from the vicinity of the nerve plexus through a side port of the distal end of the catheter introducer. Subsequently, local anesthetic may be administered to the desired nerve plexus after forwarding the catheter through the insulated needle and into the vicinity of the nerve plexus. In some cases, other fluids may be administered through a flexible tube coupled to a side port of the distal end of the catheter introducer. Generally speaking, the other fluids may be administered at any time after the step of inserting the distal end of the insulated needle through the tissue of the patient.

The method described herein provides several advantages over conventional methods for administering regional anesthesia. For example, the step of rotating the cap portion is adapted to prevent fluid leakage during the step of withdrawing the fluid, as well as during the steps of administering local anesthetic (through the catheter) or other fluids (through the side port). The current method also enables local anesthetic and other fluids to be administered without requiring components to be removed from (e.g., the flexible tubing) or attached to (e.g., a separate connector or threading assist guide) the catheter system. Thus, the current method enables a user to more easily control the catheter system, as compared to the complex manipulations required to operate conventional catheter systems. For at least these reasons, the current method advantageously minimizes movement of the catheter system after the insulated needle is inserted within the tissue of the patient.

BRIEF DESCRIPTION OF THE DRAWINGS

Other objects and advantages of the invention will become apparent upon reading the following detailed description and upon reference to the accompanying drawings in which.

Figure 1:
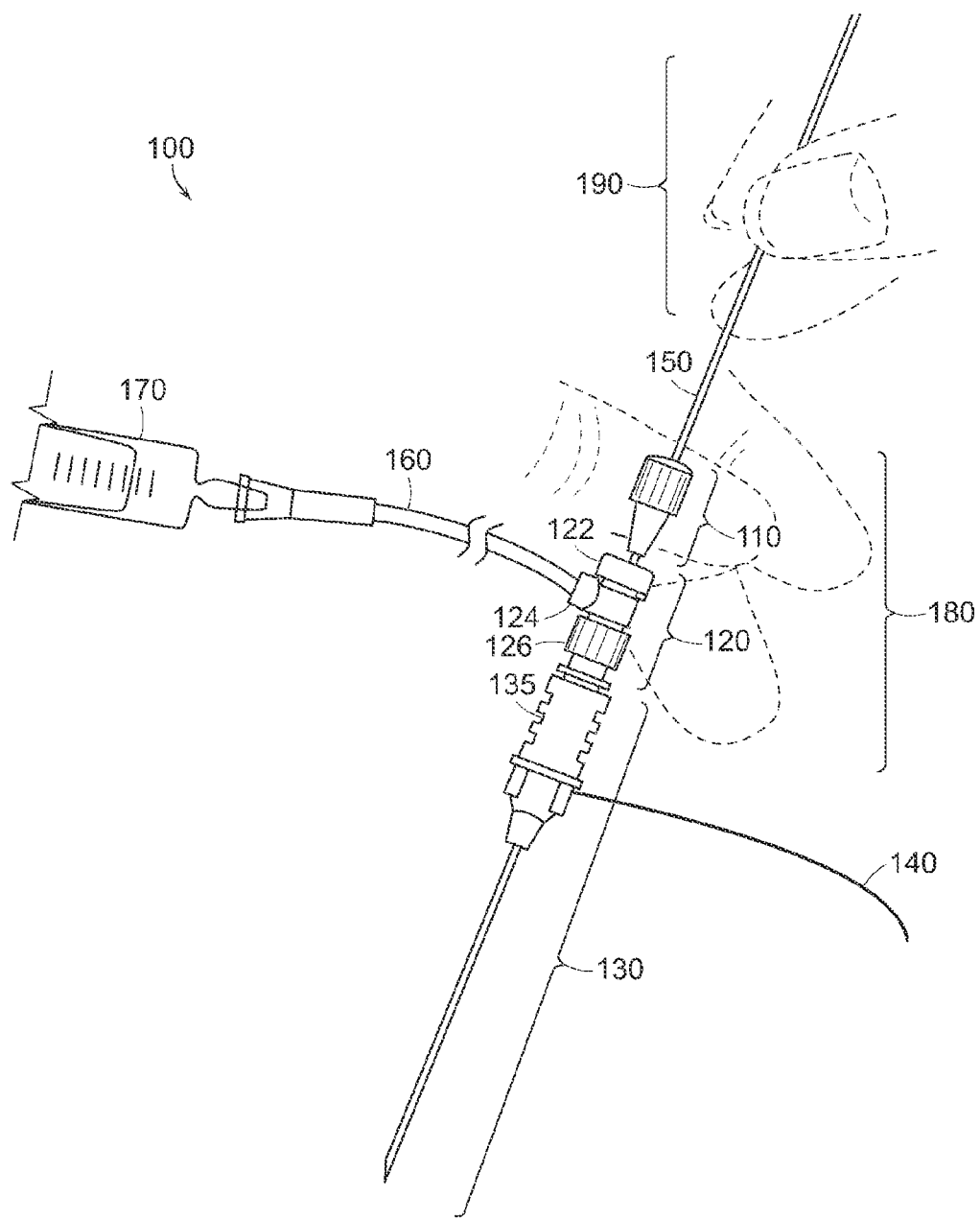
FIG. 1 is a side view of a conventional peripheral nerve catheter system.
Figure 2:
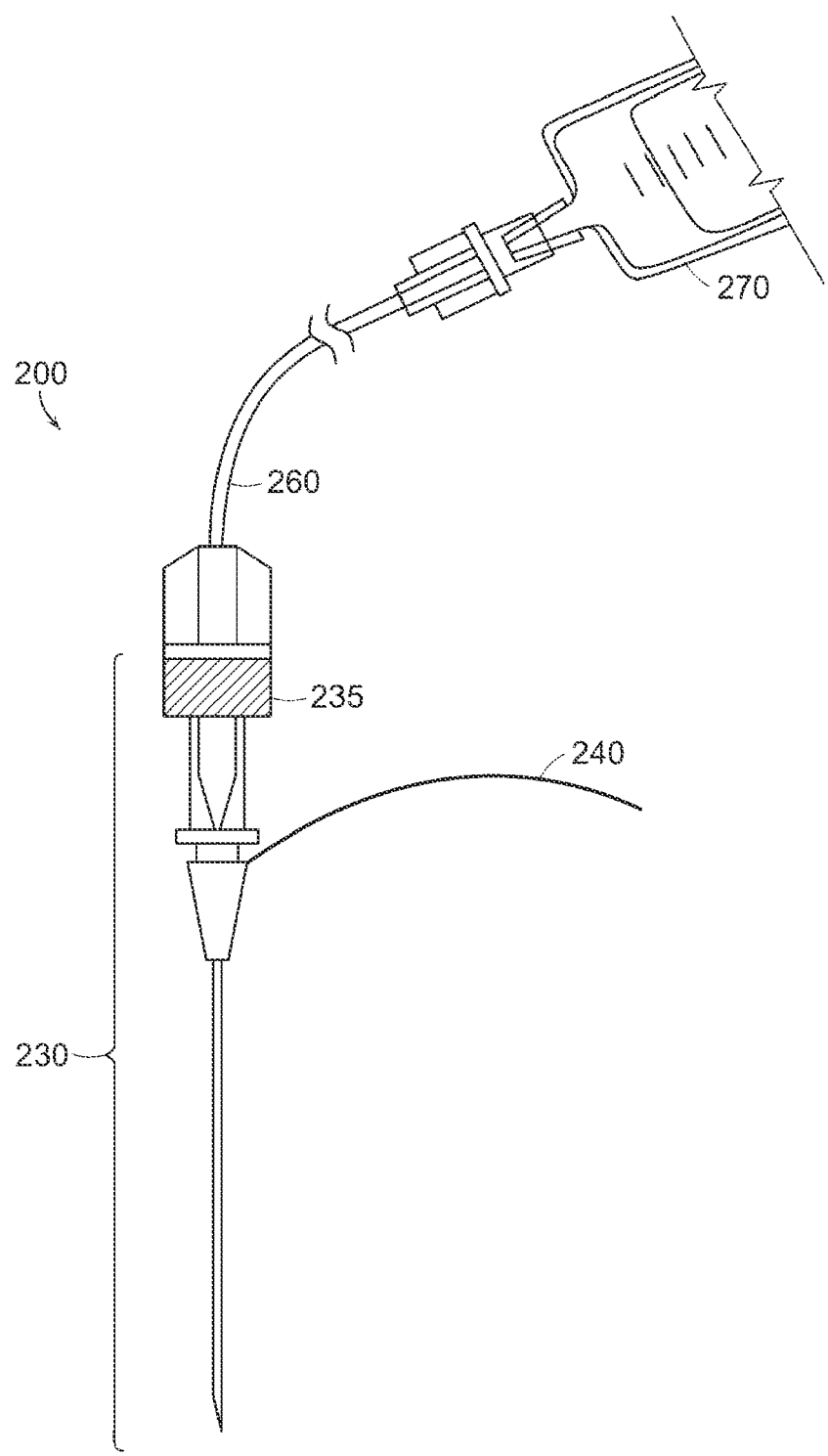
FIG. 2 is a side view of another conventional peripheral nerve catheter system.
Figure 3:
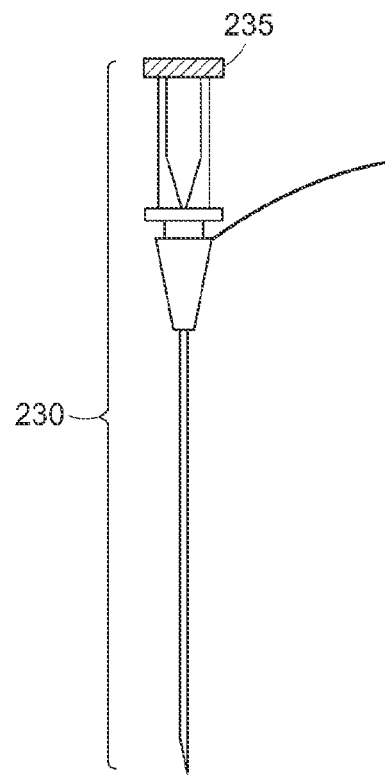
FIG. 3 is a side view of the catheter system of FIG. 2 without attached tubing, thereby exposing the proximal hub of the insulated needle.
Figure 4:
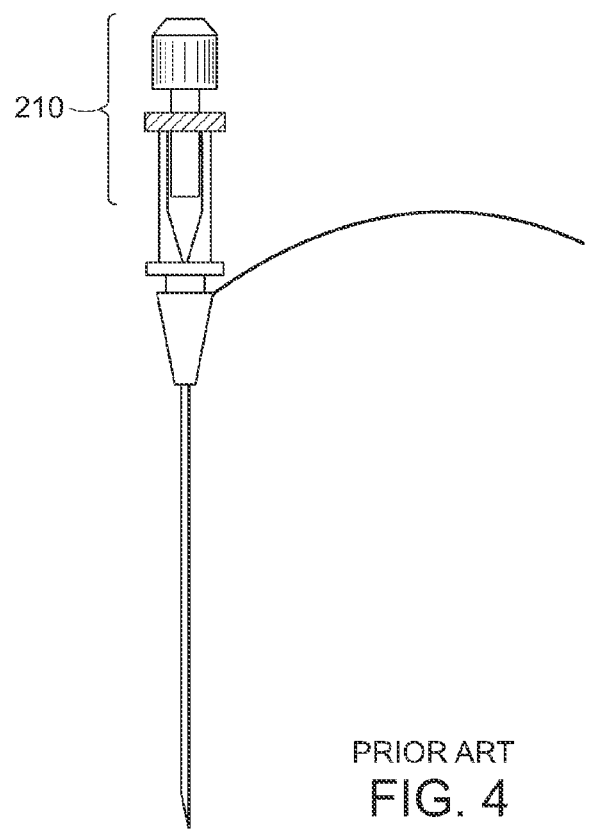
FIG. 4 is a side view of the catheter system of FIG. 3 illustrating the placement of a catheter threading assist guide into the proximal hub of the insulated needle.
Figure 5:
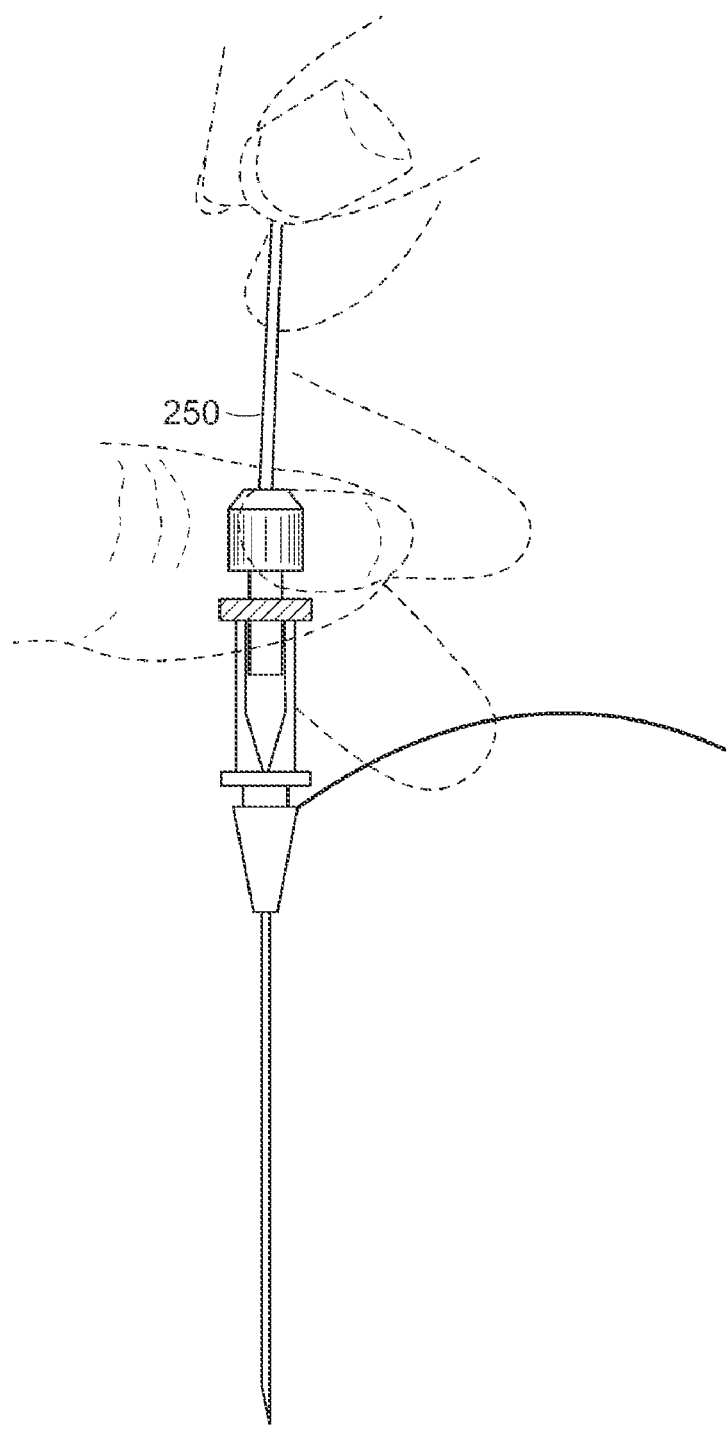
FIG. 5 is a side view of the catheter system of FIG. 4 illustrating an epidural catheter being threaded through the catheter threading assist guide.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

The present invention overcomes the shortcomings of conventional peripheral nerve catheter systems by providing an improved catheter system and method for administration of local anesthetic to achieve a desired regional anesthesia in the operative and/or post-operative setting. Unlike conventional catheter systems, the improved catheter system is configured to minimize movement of an indwelling epidural needle (due to, e.g., connecting or disconnecting of system components, such as tubing, connectors, or threading assist guides). In addition, the improved catheter system is configured, in some cases, to permit preloading of the catheter intended for administration of anesthesia, while at the same time, preventing reflux of anesthesia fluids. As will be described in more detail below, the improved catheter system is substantially easier to operate, as compared to the complex manipulations required in conventional catheter systems.

Figure 6A:
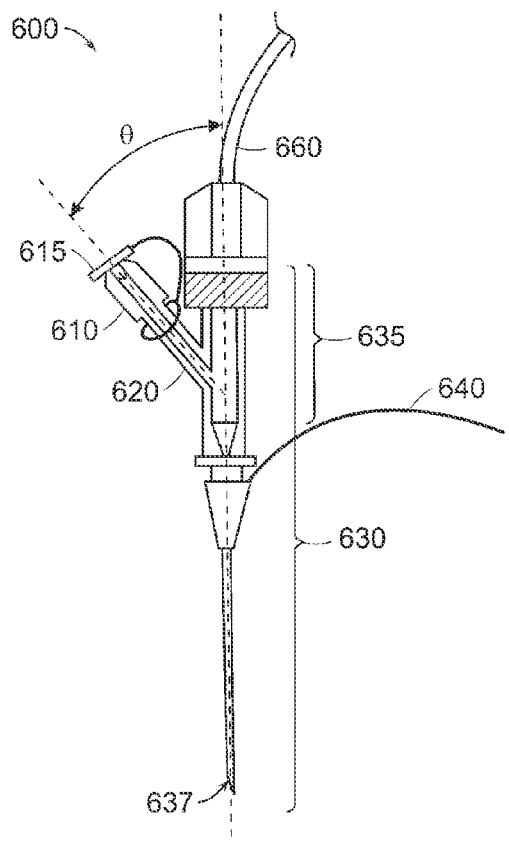
FIG. 6A is a side view illustrating one embodiment of an improved catheter system incorporating a flip-top style cap onto a catheter threading assist guide that is attached to the proximal hub of an insulated needle.

FIG. 6A illustrates one embodiment of a peripheral nerve catheter system 600 in accordance with the present invention. In this embodiment, system 600 comprises an epidural needle 630 having a proximal end 635 adapted for fluid connection and a distal end 637 adapted for insertion through tissue and into the vicinity of a desired nerve or nerve plexus within a patient. In some cases, an upper aspect of proximal end 635 (otherwise referred to as the "hub") may be configured for receiving fluids, via tubing 660, from an intravenous fluid source (not shown). Such fluids may include, for example, a dilating agent (such as a saline solution), a local anesthetic solution, or a neurolytic solution. In a preferred embodiment, the solution may be a local anesthetic employed for dilation (i.e., to create a skin wheal), as described below.

The method for locating a desired nerve or plexus of nerves is generally similar to the conventional method. In brief, the distal end 637 of the epidural needle 630 enters through the skin wheal and is gradually advanced through the tissue while milliamp levels of current are supplied to the epidural needle from a nerve stimulus device (not shown).

As such, catheter system 600 includes an electrically conductive wire 640 coupled for supplying the stimulation current to the epidural needle. Though conductive wire 640 is shown in FIG. 6A as attached to an upper aspect of distal end 637, conductive wire 640 may be alternatively attached to any conductive region of the epidural needle (and by any means possible).

Though not explicitly illustrated in FIG. 6A, epidural needle 630 is preferably insulated along the length thereof, with the exception of a lower portion (or tip) of distal end 637. Epidural needle 630 may be insulated by any means known in the art. By insulating needle 630 up to the tip of distal end 637, the stimulation current may be focused for stimulating only the desired nerve plexus. In some cases, insulated needle 630 may be a TUOHY-type needle in which the tip of distal end 637 is bent (referred to as a HUBER tip). This allows for an opening at the tip of the needle, which faces toward one side for directing a catheter to a desired location. In other cases, insulated needle 630 may have a "set tip" configuration (i.e., a straight needle with varying degrees of beveling at the distal end.). Unlike conventional catheter systems, the size of insulated needle 630 is not limited by the size of the catheter ultimately used therein. As such, insulated needle 630 may be substantially any size (and/or any length) appropriate for a given catheterization application.

In some cases, the catheter (shown in FIG. 6B) may be described as a "multi-orifice catheter", or a hollow tube having multiple openings at its distal end for administering anesthetic with a soaker-like effect. Thus, the catheter used herein may be similar to a conventional "epidural style" catheter. In other cases, however, the epidural catheter may be a "nerve stimulation catheter". In addition to having a hollow tube for administering anesthetic, such a catheter may incorporate one or more electrodes on or within an outer surface of the catheter for supplying an electrical current to surrounding tissues. Alternatively, the catheter may include any other epidural or peripheral nerve catheter known in the art. The choice of catheter may only be limited to having a size less than that of the epidural needle chosen for a particular application.

As noted above, conventional catheter systems often require connection or disconnection of one or more system components before a catheter can be threaded into the system. The necessity to connect/disconnect components may lead to a multitude of problems, such as awkward and unsafe handling of the system, and an increased possibility for fluid leakage. Attempts to connect or disconnect components while the needle is inserted within a patient may also increase the possibility for needle misplacement, which may reduce the effectiveness of the local anesthetic or increase the time needed for correctly positioning the epidural catheter. Under certain circumstances, needle misplacement may even damage the nerve if it is contacted by the needle.

The present catheter system eliminates the above problems (and possible more) by incorporating catheter threading assist guide 610 into the proximal hub 635 of the insulated needle. As will be described below, the catheter threading assist guide may be incorporated into the proximal hub in a variety of ways. In some cases, catheter threading assist guide 610 may be an integral component of a side port 620, which extends from a side surface of the proximal hub 635, as shown in FIG. 6A. Though side port 620 may extend from proximal hub 635 at substantially any angle, it may be preferred that side port 620 extend at an acute angle, θ, from a longitudinal axis of the catheter system. Generally speaking, the acute angle may consist of substantially any angle that prevents an epidural or peripheral nerve catheter (typically ranging in size between 18 and 21 gauge) from kinking upon insertion through side port 620 and into insulated needle 630. In some cases, the acute angle may be approximately 90 degrees from the longitudinal axis. In a preferred embodiment, the acute angle may consist of substantially any angle less than or equal to approximately 45 degrees from the longitudinal axis. By angling the side port in such a manner, the present catheter system reduces the possibility for interfering with, or otherwise contacting, anatomical features of the patient (such as, e.g., the patient's ear, during placement of catheters in the neck region).

In some embodiments, the catheter threading assist guide may include an end cap for sealing an orifice of the catheter threading assist guide against fluid leakage before a catheter is inserted into (or after it is removed from) the threading assist guide. Such an end cap may, therefore, be provided to prevent reflux of fluids administered through tubing 660. In the embodiment of FIG. 6A, end cap 615 is a flip-top style cap; however, end cap 615 may alternatively be hinged, screwed on, or any other type of end cap without departing in scope from the present invention. In a preferred embodiment, the end cap should be easy enough to operate so that it may be removed using only one hand and without moving the needle.

Figure 6B:
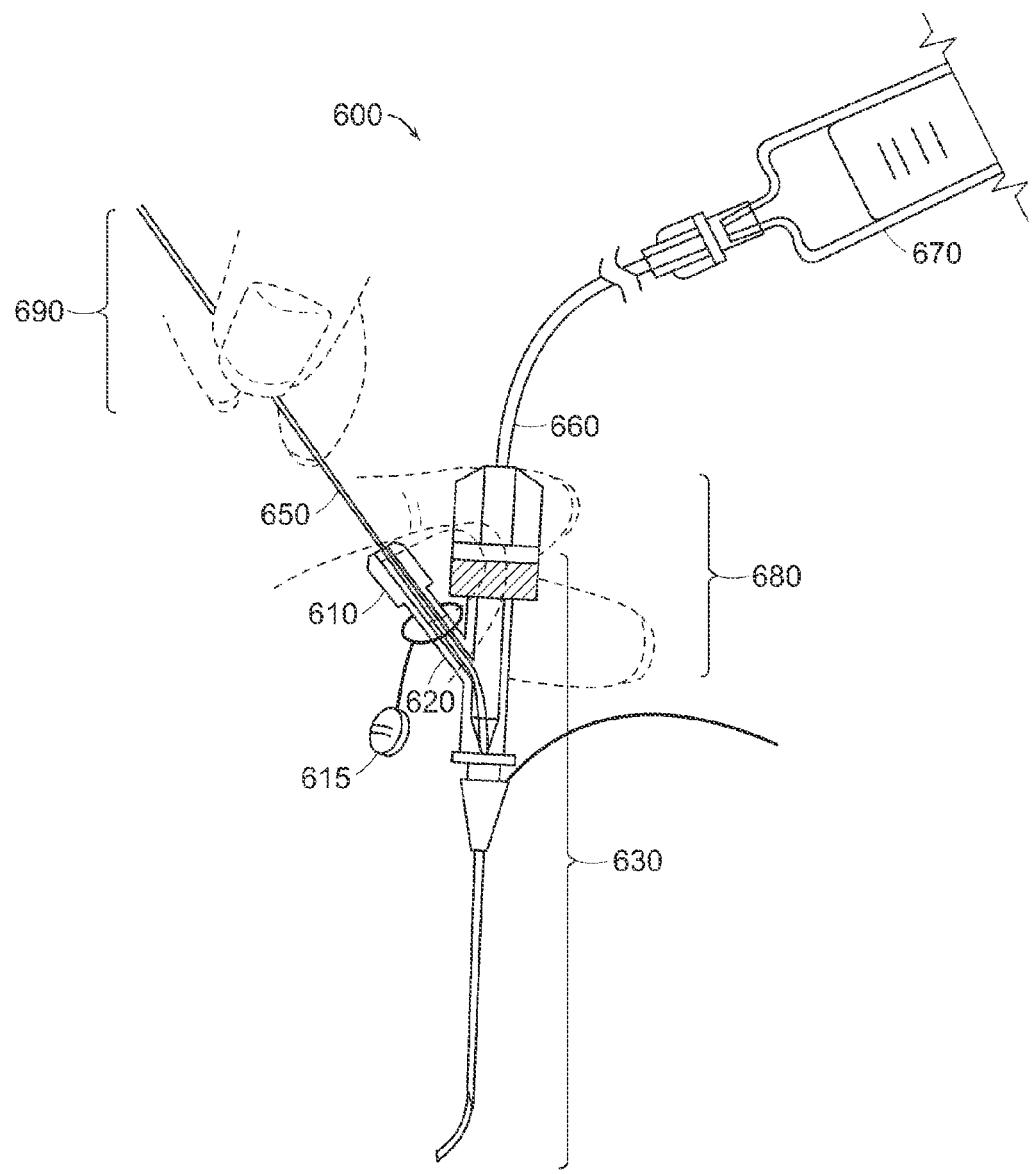
FIG. 6B is a side view illustrating the process of threading the catheter into the catheter system of FIG. 6A.

FIG. 6B illustrates the relative ease with which a user can remove end cap 615 with one hand 680, while threading catheter 650 with the other hand 690. Such ease of operation demonstrates a vast improvement over the complex manipulations required to operate most conventional catheter systems. As such, catheter system 600 substantially eliminates the problems associated with misplacement and/or movement of an indwelling needle or catheter.

The present invention also provides a convenient threading assist guide 610 for threading epidural catheter 650 into insulated needle 630 without the need to disconnect tubing 660 from anesthesia fluid source 670. In addition to reducing the possibility for needle misplacement, integration of the threading assist guide into the proximal hub advantageously reduces the number of steps needed to administer anesthesia or other fluids using the present catheter system. As shown in FIG. 6B, for example, the flip-top cap 615 may be removed after administration of local anesthetic or other fluids through tubing 660.

In some cases, tubing 660 may be conventional intravenous ("I.V.") tubing, such as commonly used in catheter systems. In a preferred embodiment, however, tubing 660 is a medical grade tubing chosen for being substantially more flexible and yielding than tubing commonly used in catheter systems. In this manner, tubing 660 may further reduce the possibility for interference with a patient's anatomical features, especially in embodiments in which the tubing is connected to a side port of the proximal hub (as shown in FIGS. 8–9). As will be described in more detail below, tubing having increased flexibility may be used to reduce such interference when coupled to an orthogonal or alternatively angled side port.

Next, epidural catheter 650 may be inserted into the orifice of the integral threading assist device 610. In some cases, catheter 650 may enter the proximal hub (via side port 620) at an angle shallow enough to prevent the catheter from kinking. As noted above, a kinked catheter may, at best, be more difficult to thread through the epidural needle. Since kinking of the catheter has the possibility to occlude the orifice of the catheter (making it nearly impossible to administer anesthesia) or cause a portion of the catheter to shear off into the patient (due to contact with a beveled edge of the needle tip), means for preventing kinking improve upon the safety of the system.

As another advantage, fingers of one hand 680 are able to hold system 600 in position so that needle 630 does not move from the desired location, while fingers of the other hand 690 are free to thread the epidural catheter 650 down threading assist guide 610 and into the tapered section of the epidural needle. The ability for fingers on hand 680 to operate flip-top cap 615, while maintaining the desired needle position in the subject's body further improves the safety of administering regional anesthesia with this system. More specifically, the process described herein for administering local anesthetic or other fluids to a desired peripheral nerve or nerve plexus (including the step of threading the epidural catheter) does not require any maneuvers, which could jeopardize correct placement of the insulated needle.

Additional embodiments, possibly having additional advantages, will be described below in reference to FIGS. 7–9. Since these embodiments are similar to the embodiment described in detail in FIG. 6, similar reference numerals will be used to describe the similar system components of FIGS. 7–9. Reference should be made to FIG. 6 for further details of the similar system components shown in FIGS. 7–9.

Figure 7A:
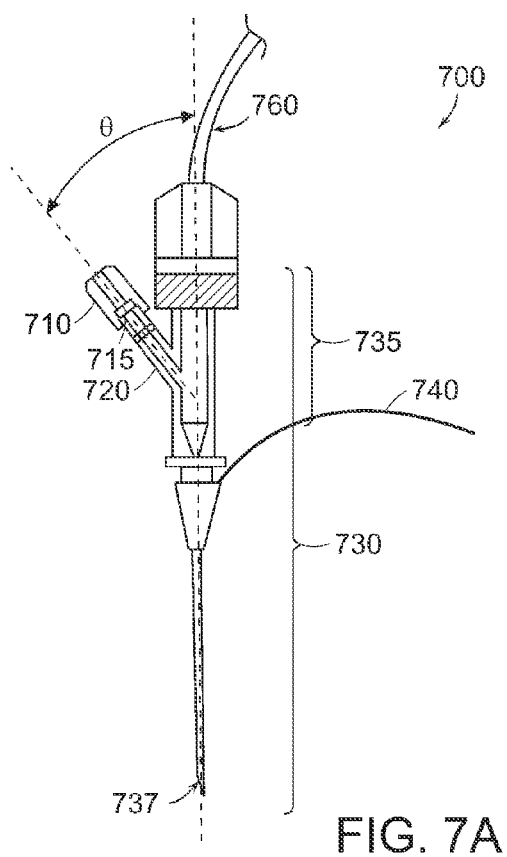
FIG. 7A is a side view illustrating another embodiment of an improved catheter system incorporating a rotational sealant element into a catheter threading assist guide that is made integral with the proximal hub of an insulated needle.

FIG. 7A illustrates another embodiment of a peripheral nerve catheter system 700 in accordance with the present invention. Similar to the embodiment of FIG. 6A, catheter system 700 includes an insulated epidural needle 730, having a proximal end 735 adapted for fluid connection to a fluid source (not shown) via tubing 760, and having a distal end 737 adapted for insertion through tissue. An electrically conductive wire 740 may also be coupled to distal end 737 for supplying an electrical current to epidural needle 730. Catheter system 700 also incorporates a catheter threading assist guide 710 into proximal hub 735 of epidural needle 730 by forming catheter threading assist guide 710 as an integral component of side port 720. As described above, side port 620 may extend from a side surface of proximal hub 735 at an acute angle, θ, to facilitate threading of the catheter without kinking.

Unlike catheter system 600, however, catheter system 700 utilizes a rotational sealant means 715 to simultaneously allow passage of the catheter while preventing any reflux that may occur during administration of anesthesia fluids. For these reasons, rotational sealant means 715 may, in some cases, be preferred over the use of end cap 615. In general, rotational sealant means 715 enables the epidural catheter to be preloaded for safer and easier administration of anesthesia fluids. Rotational sealant means 715 will be described in more detail below in reference to FIGS. 8–9.

Figure 7B:
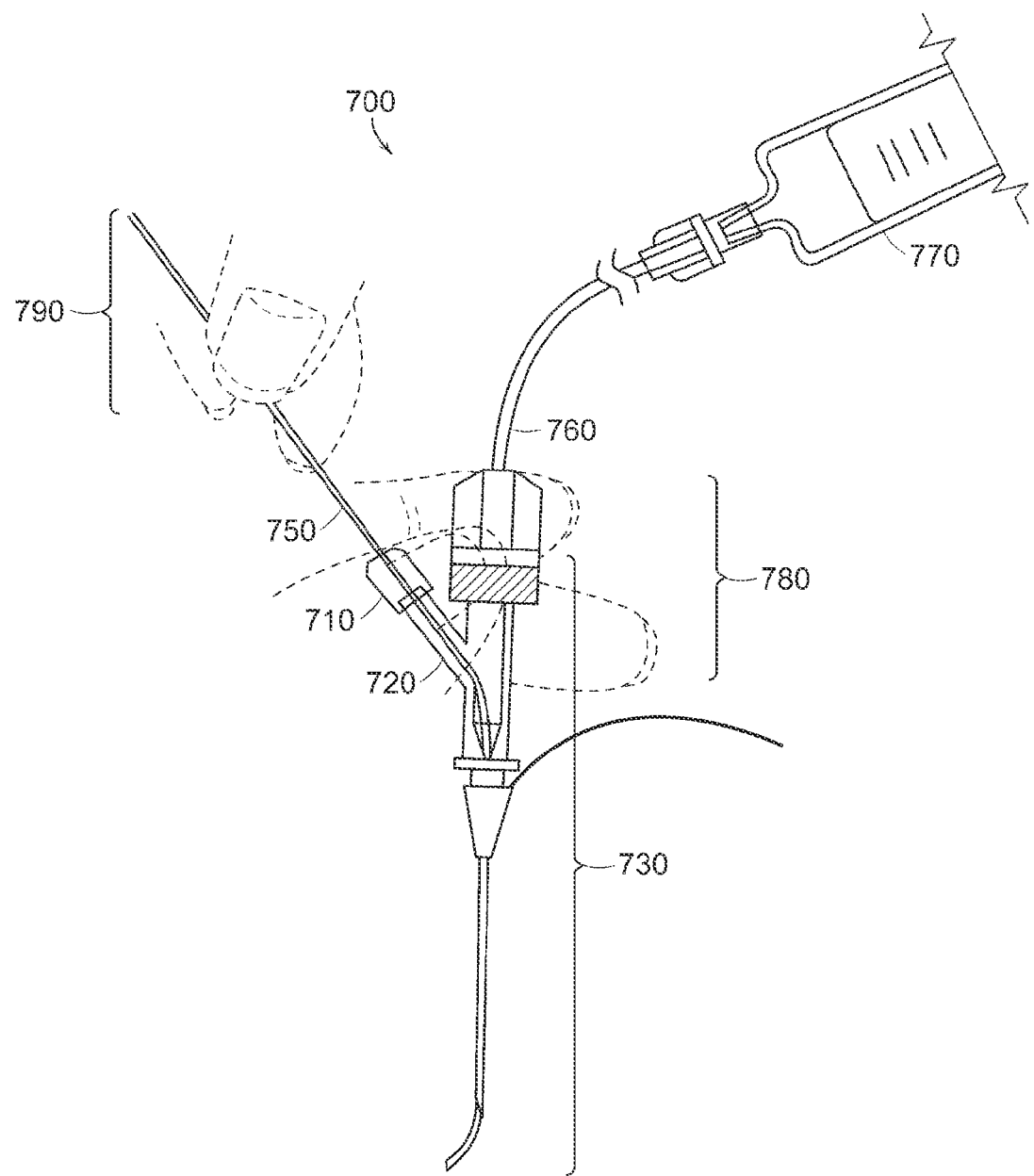
FIG. 7B is a side view illustrating the process of threading the catheter into the catheter system shown in FIG. 7A.

FIG. 7B illustrates the simplified manner with which a user can operate rotational sealant means 715 with one hand 780, while threading catheter 750 with the other hand 790. In general, epidural catheter 750 may be threaded into threading assist guide 710 substantially any time before, during, or after rotational sealant means 715 is rotated to prevent fluid leakage from system 700. This still allows the epidural catheter to pass into the proximal hub and out of the distal end of the insulated needle 730. As with the previous embodiment, catheter system 700 advantageously allows for placement of the epidural catheter with a minimum number of movements.

In general, the embodiments of FIGS. 8–9 differ from those described above by incorporating a catheter threading assist guide (otherwise referred to below as a "catheter introducer") within an upper aspect of the proximal hub, as opposed to the side port (i.e., rotational sealant means 715 of FIG. 7). Thus, the embodiments described below eliminate any possibility for kinking by enabling the catheter to be threaded down the longitudinal axis of the catheter system.

Figure 8A:
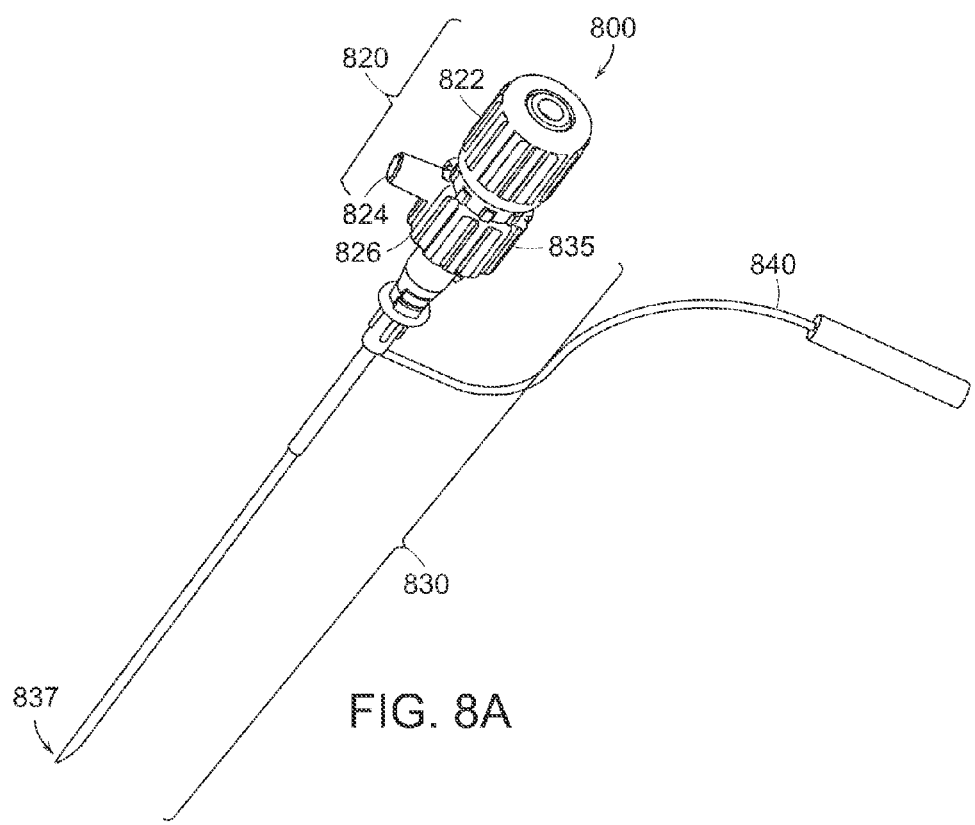
FIG. 8A is a three-dimensional view illustrating yet another embodiment of an improved catheter system incorporating a catheter introducer onto the proximal hub of an insulated needle.

In the embodiment of FIG. 8A, catheter system 800 includes a catheter introducer 820 that is incorporated into the proximal end (or hub) 835 of an insulated, epidural needle 830. As before, an electrically conductive wire 840 is attached by any means and at any location along epidural needle 830 for supplying an electrical current to the tip of distal end 837. Unlike the few known catheter systems having a catheter introducer (wherein the catheter introducer must be manually attached to the proximal hub), the catheter introducer of the present embodiment includes a distal end 826 that is made integral with the proximal hub 835 of epidural needle 830. In some cases, and as shown in FIG. 8A, the distal end 826 of catheter introducer 820 may be permanently and fixedly attached to the proximal hub 835 by an adhesive material. A suitable choice may be substantially any adhesive commonly used for adhering to plastic (or other materials chosen to form the assembled components of the catheter introducer).

Figure 8B:
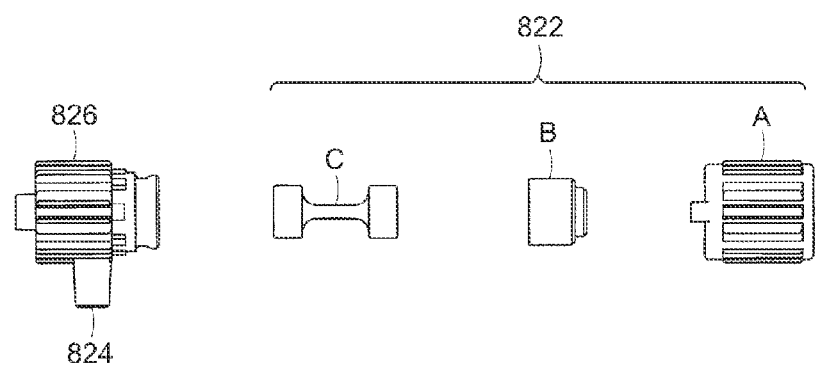
FIG. 8B is an exploded side view illustrating the internal components of the catheter introducer of FIG. 8A.

FIG. 8B is an exploded view illustrating exemplary components within catheter introducer 820. In some cases, catheter introducer 820 includes a cap portion 822A, which is in "rotational securement" with the distal end 826 of catheter introducer 820, and having a cylindrical element 822B coupled therein. One end of elastic tube 822C is fixedly attached (e.g., adhered) within cylindrical element 822B, while the other end of elastic tube 822C is fixedly attached within distal end 826. The individual components are assembled by a manufacturer of the catheter system, such that no further assembly is required on the part of a user. Once assembled, elastic tube 822C is arranged about a rotational axis (e.g., the longitudinal axis) of the integral catheter introducer and system. As such, a catheter (not shown) may enter an orifice at the proximal end of the catheter introducer to be threaded through cap portion 822A, cylindrical element 822B, elastic tube 822C, and into the proximal hub 835 of epidural needle 830.

Elastic tube 822C may be formed of substantially any material capable of a resilient elongation of approximately two fold to ten fold. In some cases, elastic tube 822C may comprise a molded medical grade silicone. In any case, elastic tube 822C may be fabricated having an internal diameter that allows passage of an epidural or peripheral nerve catheter of substantially any size. For example, the internal diameter of elastic tube 822C may be large enough to accommodate catheters ranging in size from about 18 gauge to about 12 gauge.

In this manner, the internal diameter of elastic tube 822C can be modified by simply rotating cap portion 822A relative to the distal end 826 of catheter introducer 820. In some cases, rotation of cap portion 822A may reduce the internal diameter by an amount sufficient to seal the orifice at the proximal end of catheter introducer 820 against fluid leakage before a catheter is inserted into (and/or after a catheter is withdrawn from) the catheter introducer. Though any amount of rotation may be used, it may be beneficial to configure the catheter introducer such that only a fractional rotation of the cap portion (e.g., one-quarter turn) is needed to completely seal the orifice. Such a configuration may further simplify the operation of catheter system 800.

In other cases, rotation of the cap portion 822A may reduce the internal diameter by an amount sufficient to form a continuous, fluid-tight seal about an outer surface of a catheter. Due to the resilient nature of elastic tube 822C, the integrity of the fluid-tight seal can be maintained indefinitely, if so desired. In addition, the amount of rotation needed to form the fluid-tight seal may ultimately depend on the size of catheter inserted within catheter introducer 820. As such, catheter introducer 820 is advantageously configured for maintaining the continuous, fluid-tight seal about an epidural or peripheral nerve catheter of substantially any size. The resilient nature of elastic tube 822C also enables the fluid-tight seal to be maintained about the catheter before, during and after the catheter is inserted into catheter introducer 820. Thus, catheter introducer 820 enables the catheter to be preloaded without allowing fluids to leak out of catheter system 800.

As noted above, a flexible, medical grade tubing (not shown) may be coupled to side port 824, which extends from a side surface of the distal end 826 of catheter introducer 820. Similar to side ports 620 and 720 of FIGS. 6 and 7, side port 824 may extend from distal end 826 (i.e., proximal hub 835) at substantially any angle less than or equal to 90 degrees from the longitudinal axis of the catheter system. In order to reduce interference with anatomical features of the patient, however, it may be beneficial to form side port 824 at an acute angle (e.g., any angle less than 90 degrees) from the longitudinal axis.

Figure 9A:
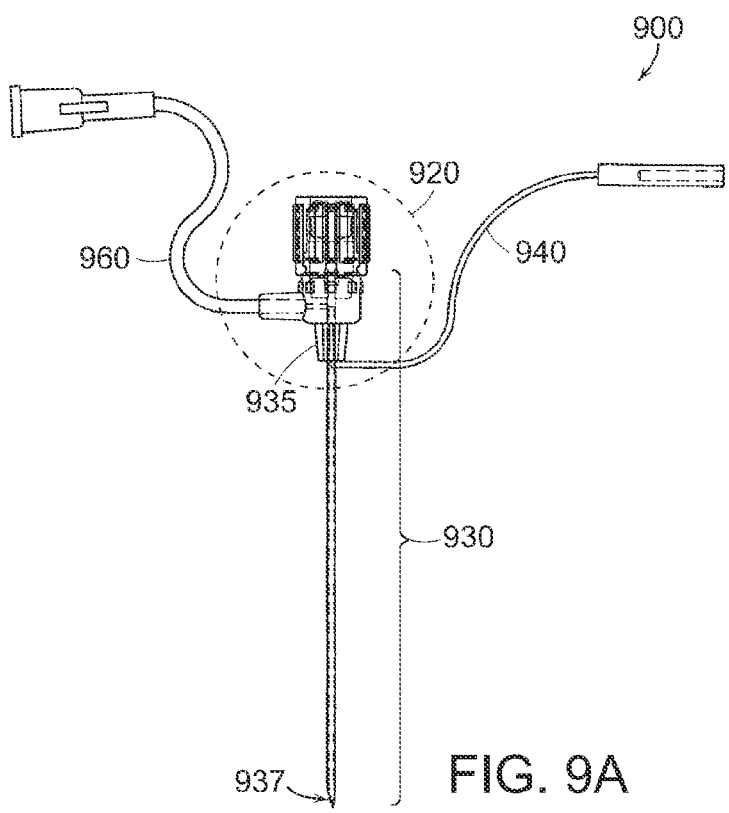
FIG. 9A is a side view illustrating yet another embodiment of an improved catheter system with a catheter introducer that is made integral with the proximal hub of an insulated needle.

FIG. 9A illustrates yet another embodiment of a peripheral nerve catheter system 900 in accordance with the present invention. Generally speaking, catheter system 900 is substantially identical to catheter system 800, and therefore, includes a catheter introducer (i.e., a catheter threading assist guide) 920 formed as an integral component with the proximal hub 935 of an insulated, epidural needle 930. An electrically conductive wire 940 is attached by any means and at any location along epidural needle 930 for supplying an electrical current to the tip of distal end 937. A flexible medical grade tubing 960 is coupled to an orthogonal side port (reference numeral 924 of FIG. 9B) for administering fluid from an optional fluid source (not shown). As before, the side port may alternatively extend from a side surface of the distal end of catheter introducer 920 at an acute angle from the longitudinal axis of the catheter system.

Figure 9B:
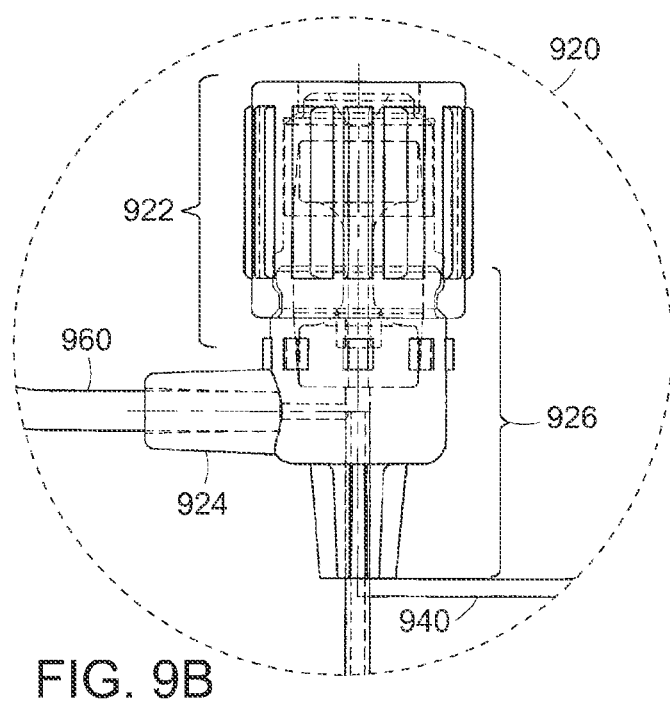
FIG. 9B is a magnified view illustrating the internal components of the catheter introducer of FIG. 9A.

As shown in FIG. 9B, the proximal hub 935 (i.e., distal end 926 of catheter introducer 920) may be formed having a reduced profile. More specifically, the overall length and/or width of proximal hub 935 may be reduced relative to the overall length and width of proximal hub 835. In addition, side port 924 may extend from a relatively lower portion of distal end 926. To achieve this "slim hub" configuration, side port 924 and distal end 926 are preferably molded onto (or as an integral part of) proximal hub 935. The molding process may be conducted by any conventional means. In some cases, the reduced profile of proximal hub 935 may further reduce interference with anatomical features of the patient. The proximal end 922 of catheter introducer 920 may include components substantially identical to those described above in FIG. 8B; thus, catheter system 900 may operate in a manner similar to catheter system 800.

Figure 10:
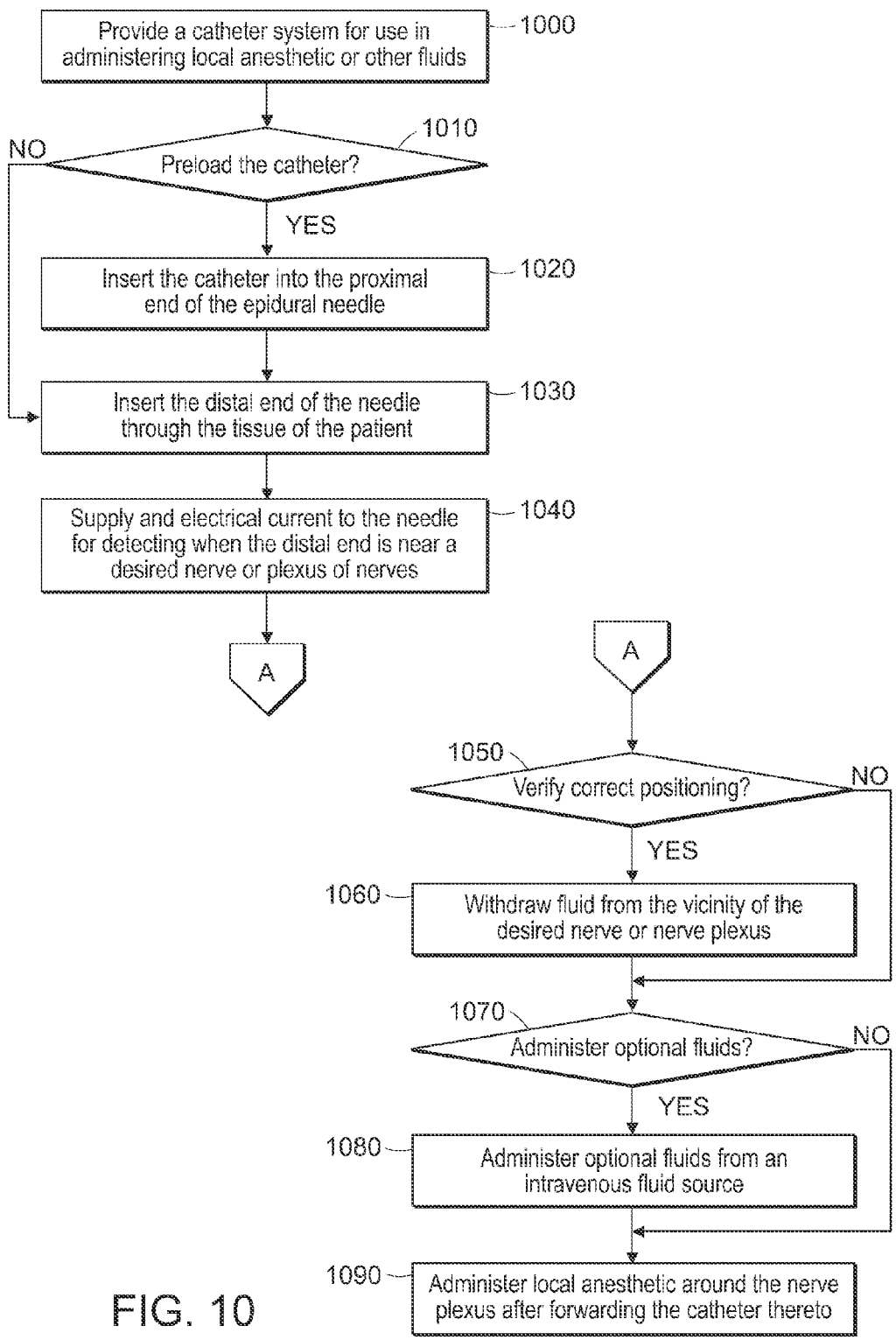
FIG. 10 is a flow chart diagram of an exemplary method for administering local anesthetic or other fluids to a nerve or plexus of nerves within a patient.

A method for administering local anesthetic or other fluids to a nerve, or plexus of nerves, within a patient may now be described in reference to FIG. 10. A catheter system, such as any of the catheter systems described above in FIGS. 6–9, may be provided in step 1000. Preferably, the catheter system utilized in the current method includes a catheter introducer (or, a catheter threading assist guide) that is integral with the proximal end of an insulated, epidural needle (as shown, e.g., in FIGS. 7–9). Regardless of the particular embodiment, the catheter system provided in step 1000 is preferably "ready to use", and therefore, requires substantially no assembly of system components (other than inserting the catheter, and connecting the flexible tubing to an intravenous fluid source, if desired).

If a user decides to preload the catheter in step 1010, the catheter is inserted into an orifice (e.g., at the proximal end or side port) of the catheter introducer and into the proximal hub of the epidural needle in step 1020. As used herein, the term "preloading" refers to the act of inserting a catheter into the catheter introducer and proximal hub before the insulated needle, or any other component of the catheter system, is inserted within the patient. By preloading the catheter, movement of an indwelling needle can be minimized when the catheter is subsequently threaded.

Before, during or after the step of preloading a catheter, the method may further include the step of rotating a cap portion of the catheter introducer (not shown). In some cases, the cap portion may be rotated to wrap an inner surface of an elastic tube within the catheter introducer around an outer surface of a preloaded catheter. As a result, an inner diameter of the elastic tube may be reduced to provide a continuous, fluid-tight seal around the outer surface of the catheter. Due, in part, to the resilient nature of the elastic tube, the catheter can be inserted into, withdrawn from, or repositioned within the elastic tube without loss of the continuous, fluid-tight seal. In cases where the catheter is not preloaded, the cap portion may be rotated to seal an orifice of the catheter introducer for preventing reflux of administered fluids.

After inserting the distal end (or tip) of the epidural needle through the tissue of the patient (step 1030), the epidural needle is gradually advanced towards a nerve or plexus of nerves responsible for detecting painful stimuli within a particular region of the patient's body. In step 1040, the user may detect when the distal end of the epidural needle is in the vicinity of a nerve or nerve plexus by supplying an electrical current to the epidural needle. For example, the needle tip may be within the vicinity of the nerve plexus (e.g., within approximately 1 mm of the nerve plexus) when the electrical current causes visible muscle contractions in the innervated area. However, the user may, in some cases, wish to verify correct positioning of the needle tip relative to the nerve plexus (step 1050). If verification is desired, fluid may be withdrawn (step 1060) from the suspected vicinity of the nerve plexus using, e.g., a syringe coupled to the flexible tubing. In this manner, the user may determine that a blood vessel has been inadvertently punctured if the aspirated fluid contains blood. The distal end of the epidural needle can then be appropriately repositioned. Regardless of the outcome, the step of rotating the cap portion substantially prevents fluid leakage during aspiration of fluids.

In step 1090, local anesthetic may be administered to the desired nerve plexus after the catheter is forwarded through the epidural needle and into the vicinity of the nerve plexus. As such, the step of rotating the cap portion prevents fluid leakage when administering local anesthetic through an indwelling catheter. In some cases (steps 1070 and 1080), other fluids may be administered through the flexible tube coupled to the catheter introducer. Though steps 1070 and 1080 are illustrated as occurring before local anesthetic is administered through the catheter (step 1090), the other fluids may be administered at any time after the distal end of the epidural needle is inserted into the patient (step 1030). As before, the step of rotating the cap portion prevents fluid leakage when administering fluids through the flexible tubing.

In addition to preventing fluid reflux, the method described herein provides several distinct advantages that were simply not addressed by conventional methods for administering regional anesthesia. In one example, the side port (having flexible tubing coupled thereto) may be configured for administration of fluids without risking needle misplacement due to contact with anatomical features of the patient. As noted above, the side port may extend at an acute angle and from a relatively lower portion of the catheter introducer to avoid such interference. Contrary to conventional methods, the current method also enables local anesthetic and other fluids to be administered without requiring components to be removed from (e.g., the flexible tubing) or attached to (e.g., a separate connector or threading assist guide) the catheter system.

By providing a catheter system with the rotational sealant means described above, the number and complexity of operational steps in the present method is significantly reduced, as compared to conventional methods. More specifically, the current method enables a user to rotate the cap portion of the rotational sealant means using only one hand, while inserting the catheter with the other hand. The rotational sealant means also allows the catheter to be preloaded within the epidural needle. For at least these reasons, the current method advantageously functions to minimize movement of an indwelling needle, thereby avoiding the dangers associated therewith.

It will be appreciated to those skilled in the art having the benefit of this disclosure that this invention is believed to provide a catheter system and method for administering local anesthetic or other fluids to a nerve or plexus of nerves. Further modifications and alternative embodiments of various aspects of the invention will be apparent to those skilled in the art in view of this description. It is intended that the following claims be interpreted to embrace all such modifications and changes and, accordingly, the specification and drawings are to be regarded in an illustrative rather than a restrictive sense.

What is claimed is:

1. A catheter system comprising:
   an insulated needle having a proximal end configured for fluid connection and a distal end configured for insertion through tissue and into a vicinity of a nerve or nerve plexus within a patient;
   an electrically conductive wire coupled for supplying an electrical current to the insulated needle;
   a catheter introducer having a distal end and a proximal end, wherein the distal end is made integral with the proximal end of the insulated needle, and wherein the proximal end of the catheter introducer comprises:
      a cap portion in rotational securement with the distal end of the catheter introducer;
      an elastic tube arranged about a rotational axis of the catheter introducer and fixedly attached to the cap portion and to the distal end of the catheter introducer;
      wherein rotation of the cap portion relative to the distal end of the catheter introducer modifies an internal diameter of the elastic tube by wrapping one end of the elastic tube about the rotational axis; and
   a catheter configured for insertion within and through the catheter introducer and the insulated needle, wherein the catheter is adapted to administer fluids within the vicinity of the nerve or nerve plexus.

2. The catheter system as recited in claim 1, wherein the proximal end of the insulated needle comprises a hub.

3. The catheter system as recited in claim 2, wherein the hub is permanently attached to the distal end of the catheter introducer by an adhesive material.

4. The catheter system as recited in claim 2, wherein the hub and the distal end of the catheter introducer are molded to form a single component of the catheter system.

5. The catheter system as recited in claim 1, wherein the proximal end of the catheter introducer comprises a catheter threading assist guide, which is permanently attached to the proximal end of the catheter introducer to facilitate threading of the catheter through the catheter introducer and the insulated needle.

6. The catheter system as recited in claim 1, wherein rotation of the cap portion reduces the internal diameter to seal an orifice of the catheter introducer against fluid leakage when the catheter is not arranged within the catheter introducer.

7. The catheter system as recited in claim 1, wherein rotation of the cap portion reduces the internal diameter to form a continuous, fluid-tight seal about the catheter when it is arranged within the catheter introducer.

8. The catheter system as recited in claim 7, wherein the catheter introducer is configured for maintaining the continuous, fluid-tight seal about the catheter before, during and after the catheter is inserted into the catheter threading assist guide.

9. The catheter system as recited in claim 7, wherein the catheter introducer is configured for maintaining the continuous, fluid-tight seal about an epidural or peripheral nerve catheter of substantially any size.

10. The catheter system as recited in claim 1, wherein the distal end of the catheter introducer comprises a side port that is coupled, through flexible tubing, to a fluid source and configured for fluid connection to the proximal end of the insulated needle.

11. The catheter system as recited in claim 10, wherein the side port extends in an orthogonal direction from a side surface of the distal end of the catheter introducer.

12. The catheter system as recited in claim 10, wherein the side port extends from a side surface of the distal end of the catheter introducer at an acute angle from a longitudinal axis of the catheter system.

13. A method for administering local anesthetic or other fluids to a nerve or plexus of nerves within a patient, the method comprising:
providing a catheter system, comprising (i) an insulated needle having a proximal end configured for fluid connection and a distal end configured for insertion through tissue and into a vicinity of the nerve or plexus of nerves, (ii) a catheter introducer having a distal end and a proximal end, wherein the distal end of the catheter introducer is either permanently attached or molded to the proximal end of the insulated needle, and wherein the proximal end of the catheter introducer comprises:
a cap portion in rotational securement with the distal end of the catheter introducer; and
an elastic tube arranged about a rotational axis of the catheter introducer and fixedly attached to the cap portion and to the distal end of the catheter introducer;
preloading a catheter within the catheter introducer and into the proximal end of the insulated needle before the insulated needle, or any other component of the catheter system, is inserted within the patient, wherein the catheter is adapted for administration of local anesthetic or other fluids; and
wherein during or after the step of preloading a catheter, the method further comprises rotating the cap portion to wrap an inner surface of the elastic tube around an outer surface of the catheter, thereby reducing an inner diameter of the elastic tube to provide a continuous, fluid-tight seal around the outer surface of the catheter, thus permitting, if desired, axial and rotational movement of the catheter within the elastic tube without loss of the continuous, fluid-tight seal.

14. The method as recited in claim 13, wherein before, the step of preloading a catheter, the method further comprises rotating the cap portion to wrap an inner surface of the elastic tube about the rotational axis of the catheter introducer, thereby reducing an inner diameter of the elastic tube to seal an orifice of the catheter introducer against fluid leakage when the catheter is not arranged within the catheter introducer.

15. The method as recited in claim 14, after the step of preloading a catheter, the method further comprising:
inserting the distal end of the insulated needle through the tissue of the patient; and
detecting when the distal end of the insulated needle is in the vicinity of the nerve or nerve plexus by supplying an electrical current to the insulated needle via an electrically conductive wire coupled thereto.

16. The method as recited in claim 15, further comprising aspirating fluid from a side port of the distal end of the catheter introducer to verify absence of blood or spinal fluid and correct positioning of the distal end of the insulated needle relative to the nerve plexus, wherein the step of rotating the cap portion prevents fluid leakage during the step of withdrawing the fluid.

17. The method as recited in claim 15, further comprising administering local anesthetic after forwarding the catheter through the insulated needle and into the vicinity of the nerve plexus, wherein the step of rotating the cap portion prevents fluid leakage during the step of administering local anesthetic.

18. The method as recited in claim 17, further comprising administering fluids to the patient through a flexible tube, which is coupled to a side port of the distal end of the catheter introducer, any time after the step of inserting the distal end of the insulated needle through the tissue of the patient, wherein the step of rotating the cap portion prevents fluid leakage during the step of administering fluids.

19. The method as recited in claim 18, further comprising providing the side port and the flexible tube with individual configurations that allow the step of administering fluids to be conducted without interference with anatomical features of the patient.

20. The method as recited in claim 19, wherein the step of administering local anesthetic and the step of administering fluids are conducted without a need for removing components from the catheter system.

21. The method as recited in claim 20, wherein the steps of rotating the cap portion and preloading the catheter function to simplify control of the catheter system by enabling a user to perform the step of rotating the cap portion using only one hand, while performing the step of preloading the catheter with the other hand.

22. The method as recited in claim 21, wherein the step of preloading the catheter, the step of rotating the cap portion, the step of providing the side port and the flexible tube, and the steps of administering local anesthetic and fluids function to minimize movement of the catheter system after the insulated needle is inserted within the tissue of the patient.

* * * * *